US009599445B2

(12) United States Patent
Ito et al.

(10) Patent No.: US 9,599,445 B2
(45) Date of Patent: Mar. 21, 2017

(54) MACHINE TOOL INCLUDING AFFECTED LAYER DETECTION SENSOR

(71) Applicant: JTEKT CORPORATION, Osaka-shi (JP)

(72) Inventors: Ryo Ito, Nagoya (JP); Naomasa Mukaide, Tokai (JP)

(73) Assignee: JTEKT CORPORATION, Osaka-shi (JP)

( * ) Notice: Subject to any disclaimer, the term of this patent is extended or adjusted under 35 U.S.C. 154(b) by 153 days.

(21) Appl. No.: 14/676,067

(22) Filed: Apr. 1, 2015

(65) Prior Publication Data

US 2015/0285609 A1 Oct. 8, 2015

(30) Foreign Application Priority Data

Apr. 7, 2014 (JP) .................................. 2014-078432

(51) Int. Cl.
*G01B 7/12* (2006.01)
*G01B 5/016* (2006.01)
(Continued)

(52) U.S. Cl.
CPC ............. *G01B 5/016* (2013.01); *B23Q 17/20* (2013.01); *B23Q 17/248* (2013.01); *B24B 5/04* (2013.01); *B24B 49/105* (2013.01); *G01N 27/90* (2013.01)

(58) Field of Classification Search
CPC .......... G01B 50/16; G01B 5/20; G01B 5/201; G01B 7/12; G01B 7/125; G01B 7/28; G01B 7/282
(Continued)

(56) References Cited

U.S. PATENT DOCUMENTS 4,514,934 A 5/1985 Ray et al.
4,903,413 A * 2/1990 Bellwood .............. G01B 7/282
33/551
(Continued)

FOREIGN PATENT DOCUMENTS

JP 2010-184343 A 8/2010
JP 201 1-01 31 4 1/2011
(Continued)

OTHER PUBLICATIONS

Extended European Search Report issued Aug. 28, 2015 in Patent Application No. 15162350.1.
(Continued)

*Primary Examiner* — G. Bradley Bennett
(74) *Attorney, Agent, or Firm* — Oblon, McClelland, Maier & Neustadt, L.L.P.

(57) ABSTRACT

A machine tool including a non-contact affected layer detection sensor capable of detecting an affected layer with high precision is provided. A machine tool includes a non-contact affected layer detection sensor, a main body, probes and that contact the surface of an workpiece, arm portions supported by the main body, and dimension measurement sensors that output a signal that corresponds to the dimension of the workpiece on the basis of displacement of the arm portions with respect to the main body. The affected layer detection sensor is provided in the arm portion, and outputs a signal that corresponds to an affected state of the workpiece. The arm portions hold the probes respectively, and are displaceable with respect to the main body in accordance with the dimension of the workpiece.

20 Claims, 4 Drawing Sheets

(51) Int. Cl.
 *B23Q 17/20* (2006.01)
 *B24B 49/10* (2006.01)
 *B23Q 17/24* (2006.01)
 *G01N 27/90* (2006.01)
 *B24B 5/04* (2006.01)

(58) Field of Classification Search
 USPC ................................ 33/501.2, 546, 550–554
 See application file for complete search history.

(56) References Cited

U.S. PATENT DOCUMENTS

| | | | | |
|---|---|---|---|---|
| 5,088,207 | A * | 2/1992 | Betsill | G01B 5/10 33/1 BB |
| 5,337,485 | A * | 8/1994 | Chien | G01B 5/201 33/550 |
| 5,918,493 | A * | 7/1999 | Cerv | B21B 38/12 33/710 |
| 6,272,762 | B1 * | 8/2001 | Kinast | G01B 5/213 33/504 |
| 6,298,571 | B1 * | 10/2001 | Dall'Aglio | B24B 5/42 33/555.1 |
| 6,430,832 | B1 * | 8/2002 | Dall'Aglio | B24B 5/42 33/555.1 |
| 6,623,332 | B1 | 9/2003 | Junker | |
| 8,429,829 | B2 * | 4/2013 | Arnold | B24B 49/045 33/555.1 |
| 8,991,064 | B2 * | 3/2015 | Trionfetti | B24B 49/045 33/552 |
| 2008/0299872 | A1 * | 12/2008 | Boselli | G01B 5/201 451/25 |
| 2010/0188035 | A1 | 7/2010 | Abeta et al. | |
| 2014/0196296 | A1 * | 7/2014 | Tu | G01B 5/30 33/556 |
| 2014/0237834 | A1 * | 8/2014 | Matsumiya | G01B 7/34 33/503 |
| 2015/0082651 | A1 * | 3/2015 | Yeh | G01B 5/201 33/831 |
| 2015/0168121 | A1 * | 6/2015 | Tait | G01B 5/008 33/503 |
| 2016/0161239 | A1 * | 6/2016 | Takanashi | G01B 5/201 33/551 |

FOREIGN PATENT DOCUMENTS

| | | |
|---|---|---|
| JP | 2011-245592 A | 12/2011 |
| JP | 2011-247631 A | 12/2011 |
| JP | 2011-252877 A | 12/2011 |
| JP | 2013-053984 A | 3/2013 |

OTHER PUBLICATIONS

Ryo Ito et al., "Development of Non-destructive Inspection System for Grinding Burn-in-process Detection of Grinding Burn", Advanced Materials Research, vol. 1017, 2014, pp. 135-140.

* cited by examiner

MACHINE TOOL INCLUDING AFFECTED LAYER DETECTION SENSOR

INCORPORATION BY REFERENCE

The disclosure of Japanese Patent Application No. 2014-078432 filed on Apr. 7, 2014 including the specification, drawings and abstract, is incorporated herein by reference in its entirety.

BACKGROUND OF THE INVENTION

1. Field of the Invention

The present invention relates to a machine tool including an affected layer detection sensor.

2. Description of the Related Art

Examples of a machine tool including an affected layer detection sensor according to the related art are described in Japanese Patent Application Publication No. 2011-245592 (JP 2011-245592 A), Japanese Patent Application Publication No. 2010-184343 (JP 2010-184343 A), Japanese Patent Application Publication No. 2011-13147 (JP 2011-13147 A), and Japanese Patent Application Publication No. 2011-252877 (JP 2011-252877 A). In JP 2011-245592 A, a wheel spindle stock is provided with an affected layer detection sensor. The affected layer detection sensor described in such documents is brought into contact with an workpiece to detect an affected layer.

Since the affected layer detection sensor contacts the workpiece, the distal end of the sensor may be worn. In contrast, performing a precise detection using a non-contact affected layer detection sensor requires reducing a gap between the sensor and the workpiece and keeping the gap constant.

SUMMARY OF THE INVENTION

It is an object of the present invention to provide a machine tool including a non-contact affected layer detection sensor capable of precisely detecting an affected layer and avoiding wear of the distal end of the sensor.

According to an aspect of the present invention, a machine tool including an affected layer detection sensor, includes:

a affected layer detection sensor of non-contact type;

a main body;

a probe that contacts a surface of an workpiece;

an arm portion which is supported by the main body, to which the probe is fixed, and which is displaceable with respect to the main body in accordance with a dimension of the workpiece; and a dimension measurement sensor that outputs a signal that corresponds to the dimension of the workpiece on the basis of a displacement of the arm portion with respect to the main body, in which the affected layer detection sensor is provided in the arm portion of the dimension measurement sensor, and outputs a signal that corresponds to an affected state of the workpiece.

The main body, the probe, the arm portion, and the dimension measurement sensor constitute a so-called sizing device. That is, the non-contact affected layer detection sensor is provided in the arm portion of the sizing device. Even in the case where the dimension of the workpiece is varied, the probe can be maintained in contact with the workpiece with the arm portion displaced with respect to the main body. With the probe contacting the workpiece, the arm portion is positioned in the vicinity of the workpiece. Thus, with the probe contacting the workpiece, the gap between the affected layer detection sensor and the workpiece is minimum, and such a gap is kept substantially constant. As a result, the affected layer detection sensor can detect an affected layer with high precision.

BRIEF DESCRIPTION OF THE DRAWINGS

The foregoing and further features and advantages of the invention will become apparent from the following description of example embodiments with reference to the accompanying drawings, wherein like numerals are used to represent like elements and wherein.

DETAILED DESCRIPTION OF EMBODIMENTS

Figure 1:
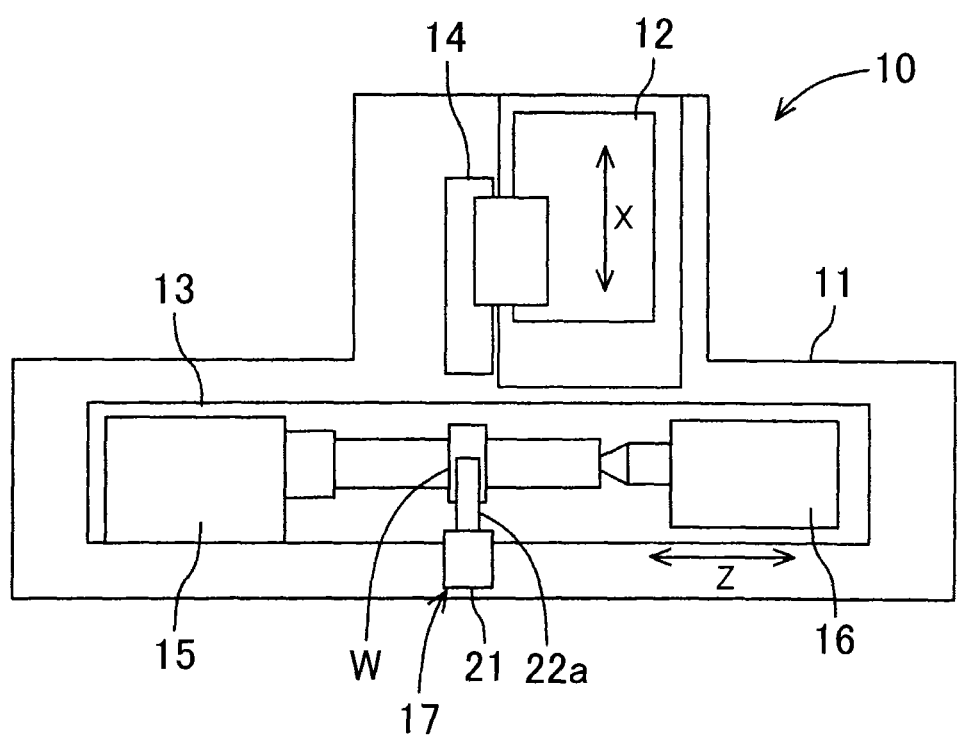
FIG. 1 is a plan view of a machine tool according to an embodiment of the present invention.

The configuration of a machine tool according to an embodiment of the present invention will be described with reference to FIG. 1. A cylindrical grinding machine 10 that grinds the outer periphery of a cylindrical workpiece W while rotationally driving the workpiece W is taken as an example of the machine tool according to the embodiment. The cylindrical grinding machine 10 includes a bed 11, a wheel spindle stock 12, a table 13, a grinding wheel 14, a main spindle 15, a tailstock 16, and a measurement unit 17.

The wheel spindle stock 12 is provided on the bed 11 so as to be reciprocally movable in the X-axis direction. The table 13 is provided on the bed 11 so as to be reciprocally movable in the Z-axis direction that is orthogonal to the X-axis direction. The grinding wheel 14 is provided on the wheel spindle stock 12, supported so as to be rotatable about an axis that extends in parallel with the Z axis, and rotationally driven by a wheel spindle rotating motor (not illustrated) provided on the wheel spindle stock 12.

The main spindle 15 is provided on the table 13, supported so as to be rotatable about an axis that extends in parallel with the Z axis, and rotationally driven by a main spindle rotating motor (not illustrated). The main spindle 15 grasps one end portion of the workpiece W. The tailstock 16 is provided on the table 13, and supports one end portion of the workpiece W.

The measurement unit 17 measures the dimension of a portion to be processed of the workpiece W, and detects an affected layer produced at the portion to be processed of the workpiece W. In the embodiment, the measurement unit 17 measures the outside diameter of the outer peripheral surface of the workpiece W, and detects an affected layer at a predetermined depth from the outer peripheral surface of the workpiece W. That is, the measurement unit 17 has a function as a sizing device and a function of an affected layer detection device.

Figure 2:
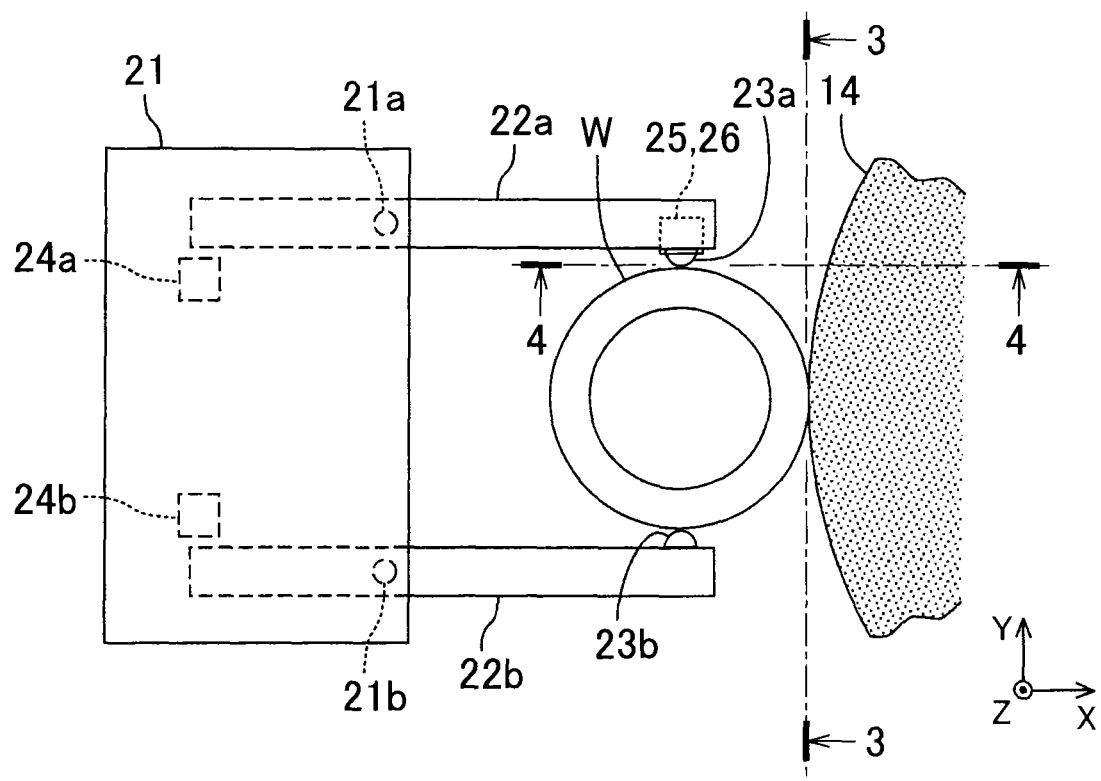
FIG. 2 illustrates a measurement unit seen from the Z-axis direction.
Figure 3:
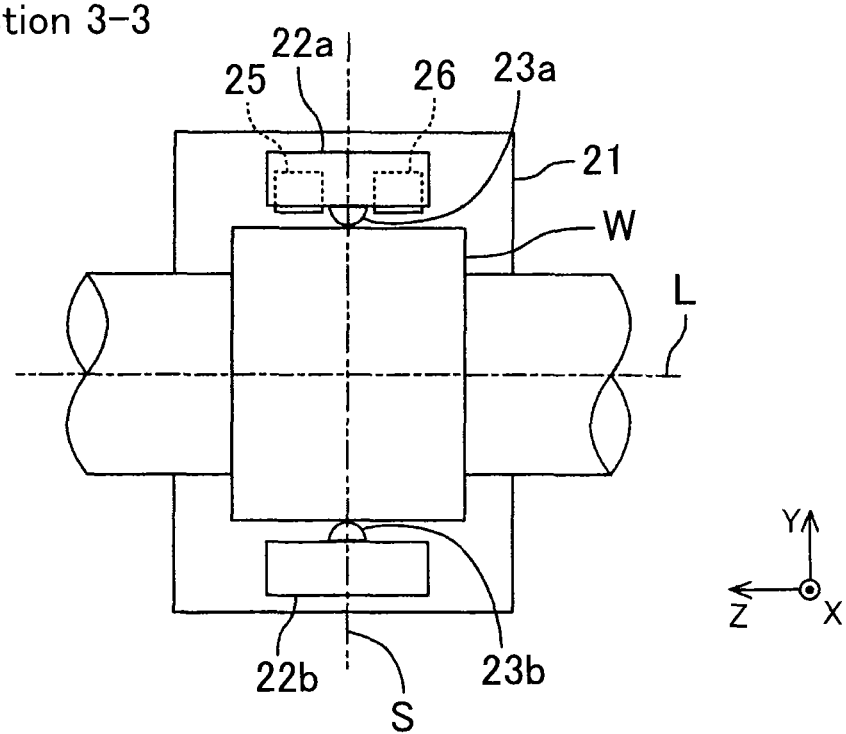
FIG. 3 is a sectional view taken along the line 3-3 of FIG. 2.
Figure 4:
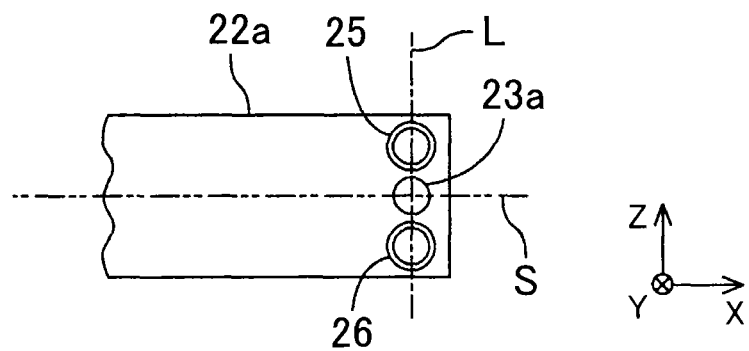
FIG. 4 is a sectional view taken along the line 4-4 of FIG. 2.

The configuration of the measurement unit 17 will be described in detail with reference to FIGS. 2 to 4. As illustrated in FIGS. 2 to 4, the measurement unit 17 includes a main body 21 provided on the bed 11, a pair of arm portions 22a and 22b, a pair of probes 23a and 23b, a pair of dimension measurement sensors 24a and 24b, a first affected layer detection sensor 25, and a second affected layer detection sensor 26. The main body 21, the pair of arm portions 22a and 22b, the pair of probes 23a and 23b, and the pair of dimension measurement sensors 24a and 24b constitute a so-called sizing device.

The arm portions 22a and 22b are supported by the main body 21 so as to be swingable about support portions 21a and 21b, respectively. The arm portions 22a and 22b are provided to project from the main body 21. The arm portions 22a and 22b extend in the X-axis direction. The arm portions 22a and 22b are disposed a certain distance away from each other in the Y-axis direction which is orthogonal to the X-axis and Z-axis directions so as to oppose each other and interpose the outer periphery of the workpiece W therebetween. That is, the arm portions 22a and 22b are disposed via a slight gap from the outer peripheral surface of the workpiece W.

The probe 23a is fixed at the distal end portion of the arm portion 22a that projects from the main body 21, and projects from the arm portion 22a toward the workpiece W (toward the other arm portion 22b). The probe 23b is fixed at the distal end portion of the arm portion 22b that projects from the main body 21, and projects from the arm portion 22b toward the workpiece W (toward the other arm portion 22a). The probes 23a and 23b are fixed at the center of the arm portions 22a and 22b, respectively, in the width direction (Z-axis direction) (FIG. 3). The respective distal ends of the probes 23a and 23b contact the surface of the outer periphery of the workpiece W.

The probes 23a and 23b are provided to oppose each other across a center axis L of the workpiece W. That is, the distance between the positions (points) at which the two probes 23a and 23b contact the workpiece W coincides with the outside diameter of the portion to be processed of the workpiece W. Thus, the arm portions 22a and 22b are displaced (swung) with respect to the main body 21 in accordance with the outside diameter of the workpiece W. Even in the case where the outside diameter of the workpiece W is varied, the probes 23a and 23b can be maintained in contact with the workpiece W with the arm portions 22a and 22b displaced with respect to the main body 21.

The dimension measurement sensor 24a is provided in the main body 21, and detects displacement (swing) of the arm portion 22a with respect to the main body 21. The dimension measurement sensor 24b is provided in the main body 21, and detects displacement of the arm portion 22b with respect to the main body 21. That is, the dimension measurement sensors 24a and 24b output a signal that corresponds to the outside diameter of the workpiece W on the basis of displacement of the arm portions 22a and 22b, respectively, with respect to the main body 21.

The dimension measurement sensors 24a and 24b may output a signal when the arm portions 22a and 22b, respectively, reach a prescribed position. In this case, the dimension measurement sensors 24a and 24b output a signal when the outside diameter of the workpiece W reaches a prescribed value. Alternatively, the dimension measurement sensors 24a and 24b may output a signal that corresponds to the position of the arm portions 22a and 22b, respectively, at all times. In this case, the dimension measurement sensors 24a and 24b output a signal that corresponds to the outside diameter of the workpiece W at all times.

The first and second affected layer detection sensors 25 and 26 detect an affected layer of the workpiece W. The first and second affected layer detection sensors 25 and 26 are each a non-contact sensor that outputs a signal that corresponds to the affected state of the workpiece W. For example, the first and second affected layer detection sensors 25 and 26 may be an eddy current detection sensor, a Barkhausen noise detection sensor, or the like known in the art. The first and second affected layer detection sensors 25 and 26 output a signal that corresponds to the affected state during a measurement by the dimension measurement sensors 24a and 24b with the probe 23a contacting the workpiece W. That is, it is possible to grasp the relationship between variations in dimension of the workpiece W and variations in affected state of the workpiece W.

The first and second affected layer detection sensors 25 and 26 are provided in the arm portion 22a of the sizing device. In particular, the first and second affected layer detection sensors 25 and 26 are provided at the distal end of the arm portion 22a (a probe 23a side end portion of the arm portion 22a). The first and second affected layer detection sensors 25 and 26 are provided via a slight gap (clearance) to the workpiece W with the probe 23a contacting the workpiece W.

With the probe 23a contacting the workpiece W, the arm portion 22a is positioned in the vicinity of the outer periphery of the workpiece W. Thus, with the probe 23a contacting the workpiece W, the gap between the first and second affected layer detection sensors 25 and 26 and the workpiece W is small, and such a gap is kept substantially constant.

More particularly, as illustrated in FIGS. 3 and 4, the first and second affected layer detection sensors 25 and 26 are disposed on the arm portion 22a such that a line that connects between the sensors 25 and 26 and the probe 23a is aligned in parallel with the center axis L of the workpiece W. Thus, the first and second affected layer detection sensors 25 and 26 are disposed around the probe 23a and at a position at which the gap from the surface of the workpiece W is minimum, and the gap between the first and second affected layer detection sensors 25 and 26 and the surface of the workpiece W is kept constant even in the case where the outside diameter of the portion to be processed of the workpiece W is varied through processing. Thus, an affected layer can be detected with high precision.

Further, the first affected layer detection sensor 25 is provided at a position away from a reference plane S to be discussed later and illustrated in FIGS. 3 and 4 in a first direction, whereas the second affected layer detection sensor 26 is provided at a position away from the reference plane S in a second direction. The reference plane S is defined as a plane that extends in parallel with the axial direction of the arm portion 22a and that includes a track of movement of the probe 23a. Particularly, the first affected layer detection sensor 25 and the second affected layer detection sensor 26 are arranged in the direction of the center axis L of the workpiece W. That is, the first affected layer detection sensor 25 and the second affected layer detection sensor 26 are disposed such that a line that connects between the center of the first affected layer detection sensor 25 and the center of the second affected layer detection sensor 26 in FIG. 4 extends in parallel with the center axis L of the workpiece W. Consequently, an affected layer that lies over a wide range in the axial direction of the workpiece W is detected at a time.

With the arrangement described above, the second affected layer detection sensor 26 functions as a balance weight that cancels or suppresses deviation from the reference plane S of the center of gravity of the arm portion 22a which includes the probe 23a and the first affected layer detection sensor 25. That is, the center of gravity of the entirety of a mobile body including the arm portion 22a, the probe 23a, and the first and second affected layer detection sensors 25 and 26 is positioned on the reference plane S. As a result, the mobile body operates stably, and the probe 23a stably contacts the surface of the outer periphery of the workpiece W. Consequently, a dimension measurement and a detection of an affected layer are performed with high precision.

That is, the second affected layer detection sensor 26 functions as a balance weight for the first affected layer detection sensor 25, and therefore the sensors 25 and 26 can balance each other in terms of weight while detecting an affected layer that lies over a wide range in the axial direction.

Output of the dimension measurement sensors and the affected layer detection sensors will be described below. As described in Japanese Patent Application Publication No. 2011-106932 (JP 2011-106932 A), for example, the first and second affected layer detection sensors 25 and 26 are provided with an eddy current detection sensor and output a signal that corresponds to the affected state of the workpiece W. An eddy current is induced in the workpiece W by an exciting current of the sensor, and an induced electromotive force due to the eddy current is varied in accordance with the affected state. Thus, an affected state is detected in accordance with the induced electromotive force.

The frequency of the exciting current of the eddy current detection sensor and the detection depth from the surface of the workpiece W are inversely proportional to each other. Thus, the sensors 25 and 26 are supplied with an exciting current at a lower first frequency (e.g. 0.5 kHz) detected at a deeper depth (e.g. about 680 μm) from the surface, and an exciting current at a higher second frequency (e.g. 250 kHz) detected at a shallower depth (e.g. about 30 μm) from the surface.

The pair of dimension measurement sensors 24a and 24b outputs a signal when the outside diameter of the workpiece W reaches values D1 and D2 set in advance. The value D1 is the outside diameter of the workpiece W at the time when the grinding process is switched from a rough grinding process to a fine grinding process. The value D2 is the outside diameter of the workpiece W when the fine grinding is ended.

Figure 5:
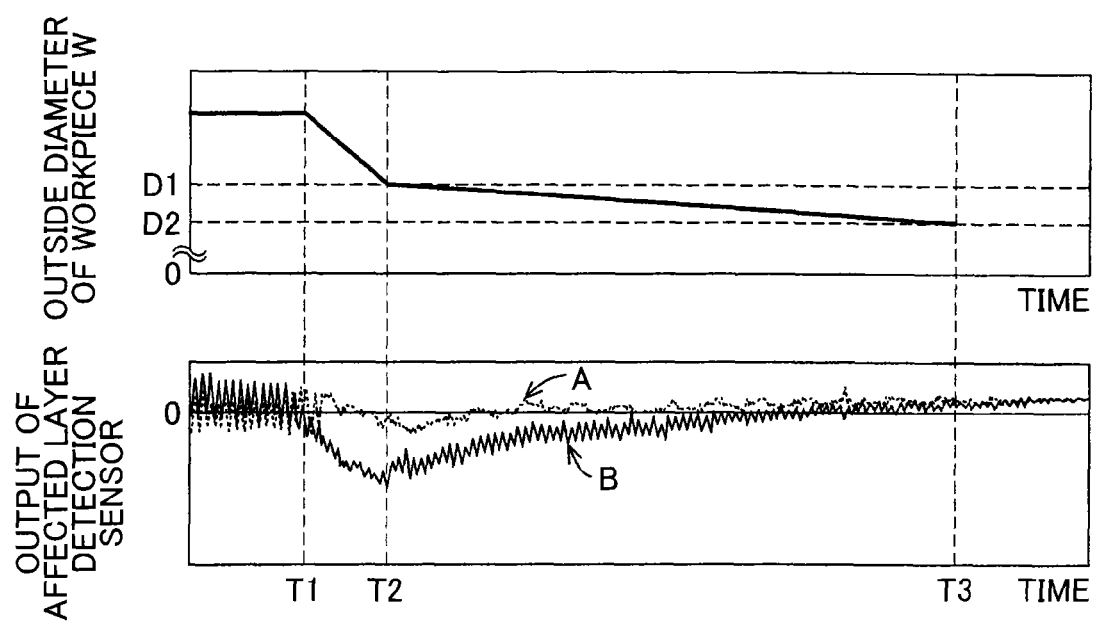
FIG. 5 indicates the outside diameter of an workpiece and an output signal from an affected layer detection sensor during processing since rough grinding until fine grinding.

The outside diameter of the workpiece W and the value of an output signal from the first affected layer detection sensor 25 obtained with the settings described above are illustrated in the upper portion and the lower portion, respectively, of FIG. 5. As illustrated in the upper portion of FIG. 5, rough grinding is started at time T1. When the outside diameter of the workpiece W reaches D1 at time T2, switching is made from the rough grinding to fine grinding. When the outside diameter of the workpiece W reaches D2 at time T3, the fine grinding is ended. In the lower portion of FIG. 5, the long dashed double-short dashed line indicated by symbol A indicates an output signal due to the exciting current at the first frequency, and the solid line indicated by symbol B indicates an output signal due to the exciting current at the second frequency.

As illustrated in the lower portion of FIG. 5, an output signal from the first affected layer detection sensor 25 is acquired during grinding performed since the start of the rough grinding until the end of the fine grinding. This enables detection of an affected layer while the workpiece W is being ground. In the lower portion of FIG. 5, only the output signal from the first affected layer detection sensor 25 is illustrated for convenience. As a matter of course, however, it is also possible to illustrate the output signal from the second affected layer detection sensor 26.

During the rough grinding from time T1 to time T2, an affected layer is produced at both the positions at a shallower depth and a deeper depth from the surface of the workpiece W. During the fine grinding from time T2 to time T3, the affected layer is reduced at both the positions at a shallower depth and a deeper depth from the surface of the workpiece W. That is, a worker can grasp variations in affected state during grinding from the start of the rough grinding until the end of the fine grinding. In particular, the first and second affected layer detection sensors 25 and 26 are provided at the arm portion 22a, and therefore an affected state is detected with significantly high precision even in the case where the outside diameter of the workpiece W is varied. That is, the worker can grasp variations in affected state with high precision.

In the embodiment described above, the measurement unit 17 measures the diameter of the outer peripheral surface (outside diameter) of the workpiece W, and detects an affected layer at a predetermined depth from the outer peripheral surface of the workpiece W. In another embodiment of the present invention, the measurement unit 17 may measure the dimension of the inner peripheral surface (inside diameter) of the workpiece W, and detect an affected layer at a predetermined depth from the inner peripheral surface of the workpiece W. In addition, the workpiece W is not limited to a cylindrical shape. Even if the workpiece W has a plate shape, the measurement unit 17 may measure the dimension of the workpiece W, and detect an affected layer at a predetermined depth from the surface of the workpiece W.

In the embodiment described above, the measurement unit 17 includes the first and second affected layer detection sensors 25 and 26. Alternatively, the measurement unit 17 may include only the first affected layer detection sensor 25, and include a simple balance weight in substitution for the second affected layer detection sensor 26. In this case as well, the mobile body is balanced.

What is claimed is:

1. A machine tool including an affected layer detection sensor, comprising:
   a affected layer detection sensor of non-contact type;
   a main body;
   a probe that contacts a surface of an workpiece;
   an arm portion which is supported by the main body, to which the probe is fixed, and which is displaceable with respect to the main body in accordance with a dimension of the workpiece; and
   a dimension measurement sensor that outputs a signal that corresponds to the dimension of the workpiece on the basis of a displacement of the arm portion with respect to the main body, wherein
   the affected layer detection sensor is provided in the arm portion of the dimension measurement sensor, and outputs a signal that corresponds to an affected state of the workpiece.

2. The machine tool including an affected layer detection sensor according to claim 1, wherein
   the affected layer detection sensor outputs a signal that corresponds to the affected state during a dimension measurement by the dimension measurement sensor with the probe contacting the workpiece.

3. The machine tool including an affected layer detection sensor according to claim 1, wherein
   the affected layer detection sensor is provided at a probe side end portion of the arm portion.

4. The machine tool including an affected layer detection sensor according to claim 2, wherein the affected layer detection sensor is provided at a probe side end portion of the arm portion.

5. The machine tool including an affected layer detection sensor according to claim 1, wherein:
    the dimension measurement sensor outputs a signal that corresponds to an outside diameter or an inside diameter of a cylindrical portion of the workpiece; and
    the affected layer detection sensor is provided in the arm portion such that a line that connects between the affected layer detection sensor and the probe is aligned in parallel with a center axis of the workpiece.

6. The machine tool including an affected layer detection sensor according to claim 2, wherein:
    the dimension measurement sensor outputs a signal that corresponds to an outside diameter or an inside diameter of a cylindrical portion of the workpiece; and
    the affected layer detection sensor is provided in the arm portion such that a line that connects between the affected layer detection sensor and the probe is aligned in parallel with a center axis of the workpiece.

7. The machine tool including an affected layer detection sensor according to claim 3, wherein:
    the dimension measurement sensor outputs a signal that corresponds to an outside diameter or an inside diameter of a cylindrical portion of the workpiece; and
    the affected layer detection sensor is provided in the arm portion such that a line that connects between the affected layer detection sensor and the probe is aligned in parallel with a center axis of the workpiece.

8. The machine tool including an affected layer detection sensor according to claim 1, wherein:
    the dimension measurement sensor outputs a signal that corresponds to an outside diameter or an inside diameter of a cylindrical portion of the workpiece; and
    the machine tool includes a plurality of the affected layer detection sensors provided in the arm portion, and the plurality of the affected layer detection sensors are arranged in a direction of a center axis of the workpiece.

9. The machine tool including an affected layer detection sensor according to claim 2, wherein:
    the dimension measurement sensor outputs a signal that corresponds to an outside diameter or an inside diameter of a cylindrical portion of the workpiece; and
    the machine tool includes a plurality of the affected layer detection sensors provided in the arm portion, and the plurality of the affected layer detection sensors are arranged in a direction of a center axis of the workpiece.

10. The machine tool including an affected layer detection sensor according to claim 3, wherein:
    the dimension measurement sensor outputs a signal that corresponds to an outside diameter or an inside diameter of a cylindrical portion of the workpiece; and
    the machine tool includes a plurality of the affected layer detection sensors provided in the arm portion, and the plurality of the affected layer detection sensors are arranged in a direction of a center axis of the workpiece.

11. The machine tool including an affected layer detection sensor according to claim 5, wherein:
    the dimension measurement sensor outputs a signal that corresponds to an outside diameter or an inside diameter of a cylindrical portion of the workpiece; and
    the machine tool includes a plurality of the affected layer detection sensors provided in the arm portion, and the plurality of the affected layer detection sensors are arranged in a direction of a center axis of the workpiece.

12. The machine tool including an affected layer detection sensor according to claim 1, wherein:
    defining a plane that extends in parallel with an axial direction of the arm portion and that includes a track of movement of the probe as a reference plane, the machine tool further comprises:
    a first affected layer detection sensor provided in the arm portion at a position vertically away from the reference plane in a first direction; and
    a balance weight that is provided in the arm portion at a position vertically away from the reference plane in a second direction opposite to the first direction and that cancels or suppresses deviation of a center of gravity of the arm portion, which includes the probe and the first affected layer detection sensor, from the reference plane.

13. The machine tool including an affected layer detection sensor according to claim 2, wherein:
    defining a plane that extends in parallel with an axial direction of the arm portion and that includes a track of movement of the probe as a reference plane, the machine tool further comprises:
    a first affected layer detection sensor provided in the arm portion at a position vertically away from the reference plane in a first direction; and
    a balance weight that is provided in the arm portion at a position vertically away from the reference plane in a second direction opposite to the first direction and that cancels or suppresses deviation of a center of gravity of the arm portion, which includes the probe and the first affected layer detection sensor, from the reference plane.

14. The machine tool including an affected layer detection sensor according to claim 3, wherein:
    defining a plane that extends in parallel with an axial direction of the arm portion and that includes a track of movement of the probe as a reference plane, the machine tool further comprises:
    a first affected layer detection sensor provided in the arm portion at a position vertically away from the reference plane in a first direction; and
    a balance weight that is provided in the arm portion at a position vertically away from the reference plane in a second direction opposite to the first direction and that cancels or suppresses deviation of a center of gravity of the arm portion, which includes the probe and the first affected layer detection sensor, from the reference plane.

15. The machine tool including an affected layer detection sensor according to claim 5, wherein:
    defining a plane that extends in parallel with an axial direction of the arm portion and that includes a track of movement of the probe as a reference plane, the machine tool further comprises:
    a first affected layer detection sensor provided in the arm portion at a position vertically away from the reference plane in a first direction; and
    a balance weight that is provided in the arm portion at a position vertically away from the reference plane in a second direction opposite to the first direction and that cancels or suppresses deviation of a center of gravity of the arm portion, which includes the probe and the first affected layer detection sensor, from the reference plane.

16. The machine tool including an affected layer detection sensor according to claim 8, wherein:
    defining a plane that extends in parallel with an axial direction of the arm portion and that includes a track of movement of the probe as a reference plane, the machine tool further comprises:
    a first affected layer detection sensor provided in the arm portion at a position vertically away from the reference plane in a first direction; and
    a balance weight that is provided in the arm portion at a position vertically away from the reference plane in a second direction opposite to the first direction and that cancels or suppresses deviation of a center of gravity of the arm portion, which includes the probe and the first affected layer detection sensor, from the reference plane.

17. The machine tool including an affected layer detection sensor according to claim 12, wherein
    a second affected layer detection sensor is provided as the balance weight.

18. The machine tool including an affected layer detection sensor according to claim 13, wherein
    a second affected layer detection sensor is provided as the balance weight.

19. The machine tool including an affected layer detection sensor according to claim 14, wherein
    a second affected layer detection sensor is provided as the balance weight.

20. The machine tool including an affected layer detection sensor according to claim 15, wherein
    a second affected layer detection sensor is provided as the balance weight.

* * * * *